United States Patent [19]

Richards

[11] Patent Number: 4,643,546
[45] Date of Patent: Feb. 17, 1987

[54] OPHTHALMOSCOPE WITH AUTOMATIC LENS SHIFTING MECHANISM

[75] Inventor: Byron A. Richards, Skaneateles, N.Y.

[73] Assignee: Welch Allyn, Inc., Skaneateles Falls, N.Y.

[21] Appl. No.: 629,191

[22] Filed: Jul. 9, 1984

[51] Int. Cl.$^4$ .............................................. A61B 3/10
[52] U.S. Cl. .................................... 351/205; 351/218
[58] Field of Search ............... 351/205, 206, 210, 211, 351/218

[56] References Cited

U.S. PATENT DOCUMENTS 2,195,169  3/1940  Graff ..................................... 351/218
2,785,598  3/1957  Kirchhubel ......................... 351/218

OTHER PUBLICATIONS

Jones, Ingenious Mechanisms for Designs and Inventions, Industrial Press, Inc., pp. 74–77, 1930.

Primary Examiner—Rodney B. Bovernick
Assistant Examiner—P. M. Dzierzynski
Attorney, Agent, or Firm—Bruns and Wall

[57] ABSTRACT

An ophthalmoscope having two lens discs one of which has three different lenses and the other of which has twenty-three different lenses. There is a viewing path through the instrument and, in use, one lens in each disc will always be in registry with the viewing passage. The two lens discs in combination provide sixty-nine different diopters ranging from −30 to +38 diopters. The lens discs have a common axis of rotation and are spaced apart so as to permit a cam plate to be positioned between the discs in close proximity to each. The cam plate is operable to provide an automatic lens shifting mechanism for the pair of lens discs.

22 Claims, 13 Drawing Figures

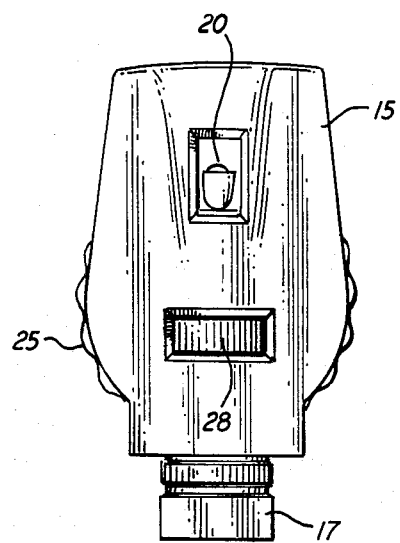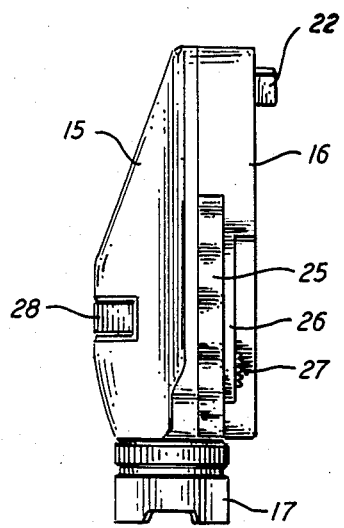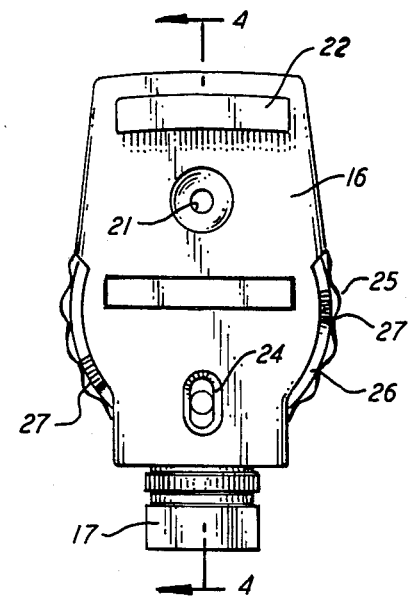
FIG. 1  FIG. 2  FIG. 3
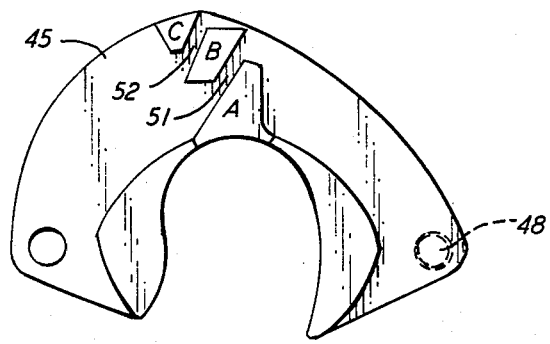
FIG. 6
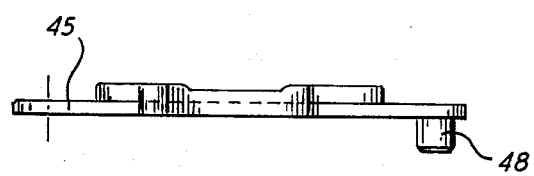
FIG. 7

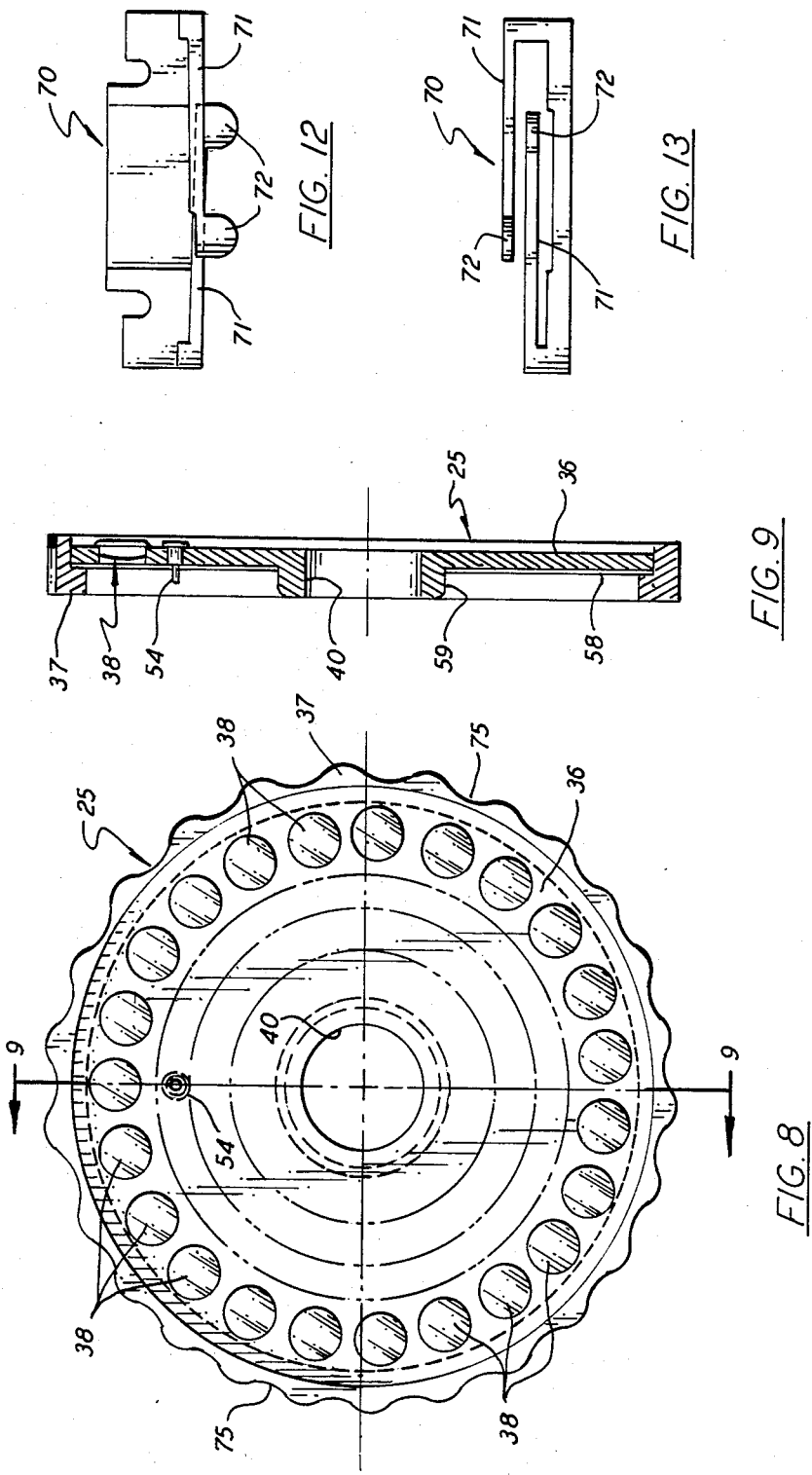

OPHTHALMOSCOPE WITH AUTOMATIC LENS SHIFTING MECHANISM

BACKGROUND OF THE INVENTION

This invention relates generally to medical diagnostic instruments, and has particular reference to an ophthalmoscope having a novel lens shifting mechanism.

In most prior art ophthalmoscopes there is a single lens disc that can be manually rotated to bring a selected one of a plurality of lenses into registry with the physician's viewing path through the instrument. Each lens has a different diopter and the physician will have as many diopter choices as there are lenses in a particular lens disc. By way of example, the applicant is aware of a commercially available ophthalmoscope having a disc with sixteen lenses and another that has a twenty-four lens disc.

It may be desirable to have a still greater choice of different lens diopters and to this end some instruments have been developed in the past that employ two lens discs, the lenses of the two discs being used in combination to increase the number of different lens diopters as where one disc acts as a "multiplier". In these instruments, to the best of applicant's knowledge, there are no automatic lens shifting mechanisms as in the present invention. The applicant is aware of an ophthalmoscope manufactured by American Optical of Southbridge, Mass. that employs two lens discs that are interconnected by a Geneva movement. However, the applicant does not know of any patent that is directed to this construction or to a construction as disclosed herein where a cam mechanism is utilized to provide an automatic lens shifting means for a pair of lens discs.

SUMMARY OF THE INVENTION

The ophthalmoscope of the invention has two lens discs one of which has three different lenses and the other of which has twenty-three different lenses. There is a viewing path through the instrument and, in use, one lens in each disc will always be in registry with the viewing passage. The three lens disc has a −23 diopter lens, a zero diopter lens and a +23 diopter lens. The twenty-three lens disc has lenses that progress from −7 diopters to a +15 diopters in one diopter steps. The two lens discs in combination provide sixty-nine different diopters ranging from −30 to +38 diopters as will be described in greater detail hereinafter.

The lens discs have a common axis of rotation and are spaced apart so as to permit a cam plate to be positioned between the discs in close proximity to each. The cam plate is pivotally connected to the ophthalmoscope housing and has two different cam surfaces that are adapted to be successively engaged by a pin on the twenty-three lens disc as the latter is manually rotated. The cam in turn has a pin that projects into a hole in the three lens disc.

When the twenty-three lens disc is rotated, its pin will, at a predetermined point, engage one of the cam surfaces on the cam plate causing the latter to pivot a relatively small, predetermined angular distance. This movement causes corresponding rotation of the three lens disc, the angular movement being sufficient to move whichever of the three lenses is in the viewing passage out of the passage and move the next adjacent lens into the passage. Thereafter, continued rotation of the twenty-three lens disc in the same direction through one complete revolution will cause its pin to engage the next adjacent cam surface which will in turn move the next adjacent lens of the three lens disc into registry with the viewing passage. The cam surfaces are designed so that the operation just described will occur regardless of the direction of rotation of the twenty-three lens disc.

In addition to its novel lens shifting mechanism, the ophthalmoscope of the invention has a unique arrangement for indicating diopter numbers using photographic film. Still another feature is a novel double detent mechanism for releasably holding a selected lens in each lens disc in registry with the viewing passage.

BRIEF DESCRIPTION OF THE DRAWINGS

FIG. 1 is a front elevation of an ophthalmoscope embodying the present invention;

FIG. 2 is a side elevation of the ophthalmoscope;

FIG. 3 is a rear elevation thereof;

FIG. 6 is an enlarged front elevation of the cam plate;

FIG. 7 is an enlarged bottom plan view of the cam plate;

FIG. 8 is an enlarged front elevation of the twenty-three lens disc assembly;

FIG. 9 is a vertical sectional view taken on line 9—9 of FIG. 8;

FIG. 12 is an enlarged front elevation of the lens detent; and

FIG. 13 is a bottom plan view of the detent.

DESCRIPTION OF THE PREFERRED EMBODIMENT

Figures 4, 5:
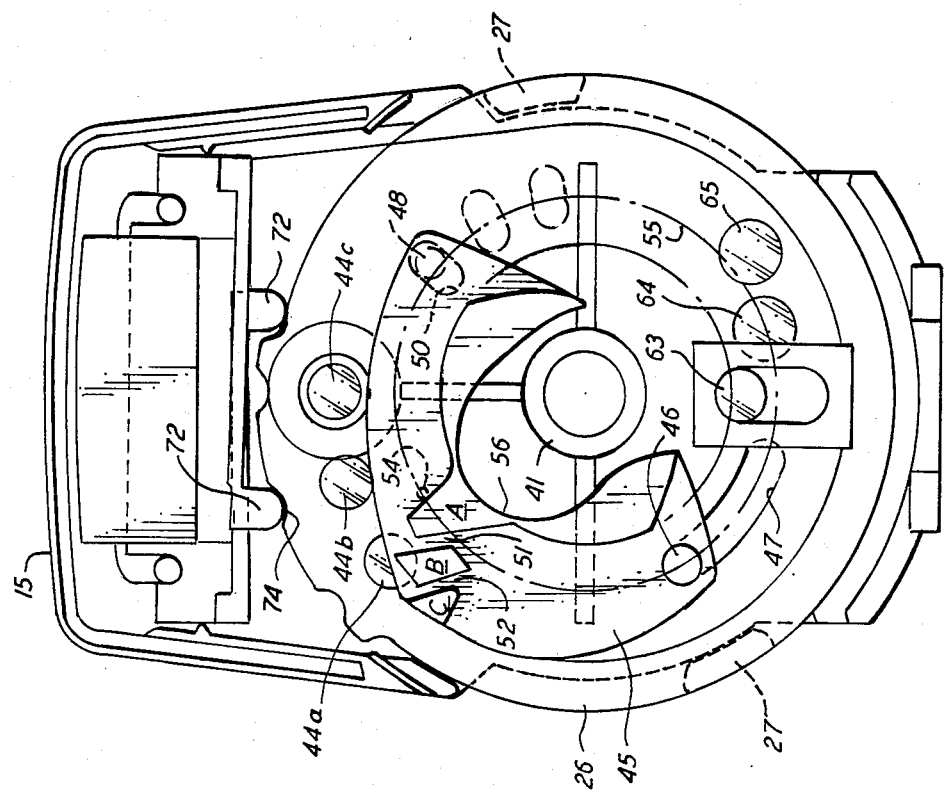
FIG. 4 is an enlarged vertical sectional view through the ophthalmoscope taken substantially on line 4—4 of FIG. 3.
FIG. 5 is a vertical sectional view through the ophthalmoscope taken on line 5—5 of FIG. 4, with the twenty-three lens disc assembly removed.

Having reference now to the drawings, and with particular reference to FIGS. 1-3, the ophthalmoscope includes a main body portion 15 and a mating cover 16 which together form the housing for the instrument. The body portion 15 has a neck 17 that is adapted to be releasably connected to a conventional battery handle (not shown). A viewing passage, indicated by the phantom line 18 in FIG. 4, extends transversely through the instrument and this passage terminates at the front of the instrument in an opening 20 and at the rear of the instrument in an opening 21.

At the rear of the instrument there is a resilient bumper element 22, FIGS. 2 and 3, of rubber or the like that engages the physician's brow as he looks through the viewing passage 18. Below the viewing passage opening 21 at the rear of the instrument there is a window 24 for indicating the diopter of the lens combination positioned in the viewing passage as will be described in more detail hereinafter. In accord with the invention, the ophthalmoscope has two rotatable lens discs 25 and 26, FIGS. 1-3. Disc 25 has a scalloped edge as shown so that the physician can turn it easily with his finger. Lens 26 is normally automatically shifted by lens 25, as will be explained, but is provided with a pair of serrated lugs 27 for manual over-ride. At the front of the instrument there is access to an aperture selection disc 28 of conventional construction.

The ophthalmoscope is provided with a lamp 30, FIG. 4, that receives power from batteries in the battery handle. Light rays emitted by this lamp pass through a condensing lens 31 and an objective lens (not shown) and focus on a 45° angle mirror 32 in a well known manner. The mirror directs the light out through the front opening 20 into the eye of the patient, the light path being substantially parallel and as close as possible to the physician's line of sight through the viewing passage 18. Some of the rays emitted by the lamp 30 also pass through an opening 34 in an interior wall 35 of the instrument and then through the lens discs 25,26 and window 24 to illuminate the lens diopter number as will be explained in more detail hereinafter.

Lens disc 25, FIGS. 4, 8 and 9, is an assembly comprised of a central, transparent disc element 36 and a rim 37 that is secured to the disc element as by ultrasonic welding. The disc element has a total of twenty-three circumferentially disposed lenses 38, the element being preferably of plastic and the lenses being molded therein with optical precision. The lenses progress from −7 diopters to +15 diopters in one diopter steps. Disc element 36 has a central opening 40 which receives and is freely rotatable on a hollow hub 41, FIG. 4, that projects from the inner wall of the cover 16.

Figure 11:
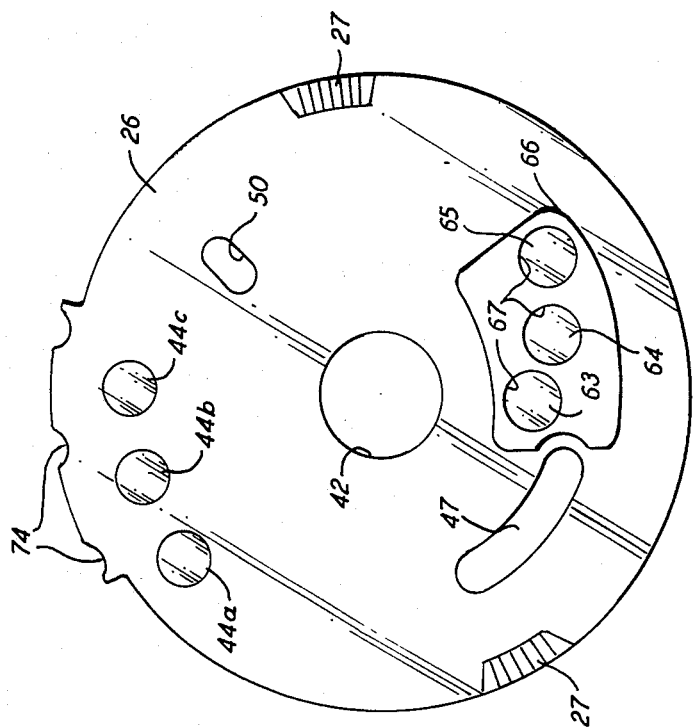
FIG. 11 is an enlarged rear elevation of the three lens disc.

Lens disc 26, FIGS. 4, 5 and 11, is also made of transparent plastic and is formed with a central opening 42 to permit it to be rotatably mounted on the hub 41 as shown in FIG. 4. Disc 26 has only three diopter lenses 44a, 44b and 44c which are spaced a short distance from one another in a relatively narrow sector of the disc as best shown in FIG. 11. The lens 44a is a −23 diopter lens, lens 44b is a zero diopter lens and lens 44c is a +23 diopter lens.

A cam plate 45, FIGS. 4–7, is positioned between the lens discs 25 and 26, the plate being pivotally connected to the instrument cover 16 by a pin 46, FIG. 5. Because the lens disc 26 is located between the cam plate and cover, the disc is provided with an arcuate slot 47, FIGS. 5 and 11, through which the pivot pin 46 passes, the slot permitting limited rotation of the disc 26 relative to the fixed pin. The cam plate is provided with a rearwardly projecting pin 48, FIGS. 5–7, which is received in a radially disposed slot 50 in the lens disc 26 whereby the cam plate and disc are loosely connected together.

As best shown in FIGS. 5 and 6, the cam plate 45 has three raised cam surfaces A, B and C with channels 51 and 52 between adjacent cam surfaces. The twenty-three lens disc 25 carries a rearwardly projecting pin 54, FIGS. 4, 5, 8 and 9, that moves into engagement with these cam surfaces as the disc 25 is rotated. Thus, with the three lens disc 26 positioned as shown in FIG. 5 and the cam plate positioned as shown in the same Figure, rotation of the disc 25 in the clockwise direction will cause its pin to follow a path indicated by the phantom lines 55 until it comes into contact with the left side of cam surface A.

With continued rotation of lens disc 25, the pin 54 will push against cam surface A which will in turn cause the cam plate 45 to pivot in the clockwise direction about its pivot pin 46. This will continue until the rotating pin has pivoted the cam plate far enough to enable the pin to clear the upper left corner of cam surface A at which time the pin will cease to engage the cam surface and there will be no further pivotal movement of the cam plate. When the cam plate is pivoted as just described, its pin 48 in engagement with the slot 50 in lens disc 26 causes the latter to rotate clockwise an angular amount sufficient to move lens 44c out of the viewing passage of the instrument and to move the next adjacent lens 44b into registry with the viewing passage.

The described pivotal movement of cam plate 45 in addition to moving cam surface A out of the path 55 of pin 54 will move cam surface B into the path, FIG. 5. Continued clockwise rotation of the lens disc 25 through one complete revolution will therefore bring the pin into contact with the left side of cam surface B. With continued rotation, the pin will push against the cam surface causing the cam plate to pivot in the clockwise direction until the pin clears the upper left corner of cam surface B and there is no further pivotal movement of the cam plate.

This further increment of pivotal movement of the cam plate 45, FIG. 5, causes its pin 48 to further rotate lens disc 26 in the clockwise direction through an angular amount sufficient to move lens 44b out of the viewing passage and to move lens 44a into registry with the passage. The pivotal movement of the cam plate in addition to moving cam surface B out of the path of pin 54 will move cam surface C into the path. Thereafter, continued clockwise rotation of the lens disc 25 through another revolution will bring its pin into contact with the cam surface C at which time further clockwise rotation of the lens discs will be prevented by engagement of the pin 46 with the end of slot 47, FIG. 5.

When the pin 54 has come to a stop against the left side of the cam surface C as described above, counterclockwise movement of the lens disc 25 will reverse the entire procedure, successively moving the lenses 44b and 44c of lens disc 26 back into registry with the viewing passage. Thus, counterclockwise rotation of the disc 25 will bring its pin 54 into contact with the right side of cam surface C and continued rotation will cause the pin to push against the surface which will cause the cam plate to pivot in the counterclockwise direction. At some point in the pivotal movement of the cam plate the pin 54 will move along the channel 52 between cam surfaces B and C and there will be no further movement of the cam plate.

The above described counterclockwise pivotal movement of the cam plate will result in corresponding counterclockwise movement of the lens disc 26 sufficient to move lens 44a out of the viewing passage and to move lens 44b into registry with the passage, the lens movement being due to the pin 48 and slot 50 connection between the cam plate and lens. The described pivotal movement of the cam plate in addition to moving the cam surface C out of the path 55 of pin 54 will move cam surface B into the path. Thereafter, continued counterclockwise rotation of lens disc 25 brings the pin into engagement with the right side of cam surface B which will cause a further increment of counterclockwise pivotal movement of the cam plate 45 and bring lens 44c into registry with the viewing passage. Eventually pin 54 will contact the right side of cam surface A, as shown in FIG. 5, and stop its counterclockwise rotation.

Since the physician may wish to shift lenses in the three lens disc 26 without having to rotate lens disc 25 through one complete revolution, the disc 26 is provided with a pair of serrated lugs 27 adjacent its periphery, FIGS. 2, 3 and 5. These lugs can be used by the physician to effect a manual over-ride.

If the lens disc 26 is positioned so that its −23 diopter lens 44a is in the viewing passage and the lens disc 25 is positioned so that its −7 diopter lens is in the viewing passage, the lens combination will be −30 diopters. Rotation of the disc 25 one lens at a time will change the reading to −29, −28, −27 diopters, etc. until the disc 25 has rotated through one lens short of a complete revolution at which time its +15 diopter lens will be in the viewing passage and the lens combination will be −8 diopters. Further rotation of disc 25 one further lens step will again bring its −7 diopter lens in the viewing passage and at the same time lens disc 26 will be shifted as previously described bringing its zero diopter lens into registry with the viewing passage. The lens combination will then be at −7 diopters.

Continued rotation of lens disc 25 in the same direction will successively change the reading to −6, −5, −4 diopters, etc. until the disc 25 has rotated through one lens short of a complete revolution at which time its +15 diopter lens will be in the viewing passage and the lens combination will be +15 diopters. Further rotation of disc 25 one further lens step will again bring its −7 diopter lens in the viewing passage and shift lens disc 26 so that its +23 diopter lens is in the viewing passage whereupon the lens combination will be +16 diopters. Further rotation of lens disc 25 in the same direction will successively change the reading in one diopter steps until the +15 diopter lens is in the viewing passage and the lens combination will be at +38 diopters. This is the highest diopter possible in the embodiment of the invention disclosed and the lens disc 25 cannot be rotated further in the same direction.

As noted hereinabove, the physician can read the diopter numbers of a particular lens combination through a window 24 at the rear of the instrument, FIGS. 3-5. These numbers appear on a disc shaped piece of film 58, FIGS. 4 and 10, that overlies the rear side of lens disc 25 as best shown in FIGS. 4 and 9, the film disc having a central hole 60 to accommodate the hub 59. Adjacent its periphery, the film disc 58 has twenty-three circular holes 61, FIG. 10, which register with the lenses 38 in the lens disc 25.

Figure 10:
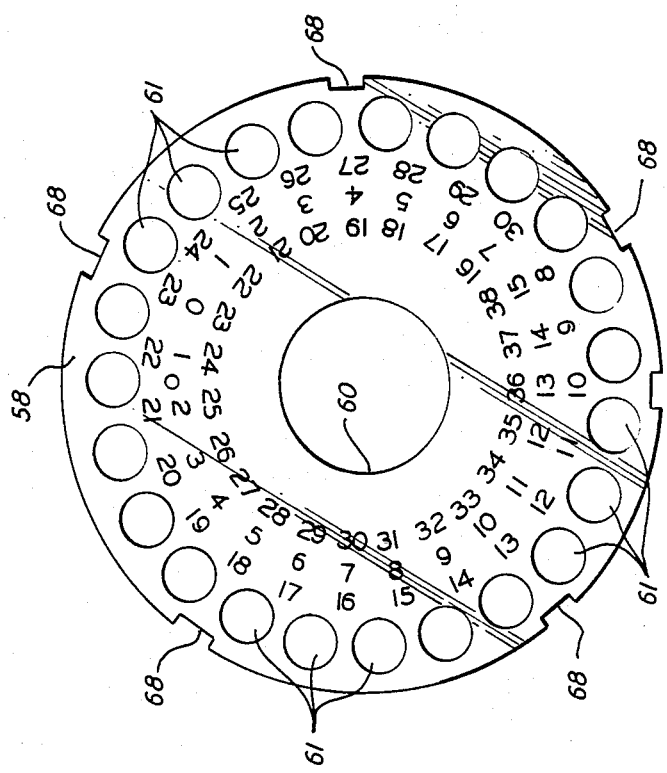
FIG. 10 is an enlarged elevation of the film bearing the lens diopter numbers.

The film disc 58 is essentially opaque but the diopter numbers are clear or translucent so that light rays from the lamp 30, FIG. 4, will pass through them making the numbers visible through the window 24. The diopter numbers are arranged in three concentric rows as best shown in FIG. 10 and range from −30 to +38 to correspond to the range of possible diopters provided by the two lens discs 25 and 26. As is conventional, the diopter numbers are diametrically opposite the lenses they represent.

Lens disc 26 is clear plastic and has three magnifying lenses 63, 64 and 65 through which the different rows of diopter numbers can be viewed. However, so that only one row of diopter numbers will be visible at a time through the window 24 an opaque light baffle 66, FIG. 11, is secured to the lens disc, the baffle having three windows 67 that are coincident with the magnifying lenses. The windows 67 are at different radial distances from the center of the film to correspond with the radial spacing of the diopter number rows. The windows are also angularly offset from one another by an angular amount that is the same as the spacing between lenses 44a, 44b and 44c.

With this arrangement, as can be seen from FIG. 5, when the +23 diopter lens 44c of the disc 26 is in the viewing passage, the lens 63 will be in registry with the diopter indicator window 24 permitting only the inner row of diopter numbers on the film disc to be seen, these being the consecutive diopter numbers from +16 to +38. Similarly, when the zero diopter lens 44b is moved into the viewing passage, the lens 64 will move into registry with the window 24 permitting only the middle row of diopter numbers to be seen, these being the consecutive diopter numbers from +15 to −7. Movement of the −23 diopter lens 44a into the viewing passage will cause the lens 65 to move into registry with the window 24 whereby only the outer row of diopter numbers can be seen, these being the consecutive numbers from −8 to −30 diopters. To assist the physician, the positive diopter numbers can be tinted green and the negative numbers red with the $\phi$ diopter number being clear. To properly locate the film disc 58 relative to the underlying lens disc 25, the disc is provided with peripheral locator recesses 68, FIG. 10, that mate with conforming lugs (not shown) on the lens disc.

The lenses 38 of the lens disc 25 and lenses 44a, 44b and 44c of the lens disc 26 are releasably held in registry with the viewing passage 18 through the instrument by a spring detent 70 located in the upper part of the instrument directly above the lens discs, FIGS. 4, 5, 12 and 13. The detent 70 is a unitary, resilient member having two substantially parallel arms 71 each of which has a rounded protuberance 72 at its free end. As best shown in FIG. 5, the protuberance 72 on one arm is spring biased into engagement with one of three conforming peripheral recesses 74 on the lens disc 26, FIGS. 5 and 11, while the protuberance on the other arm is spring biased into engagement with one of a series of conforming peripheral recesses 75 on the lens disc 25, FIGS. 5 and 8. As shown in FIG. 8, there are twenty-three recesses 75 to correspond to the twenty-three lenses 38 in the disc. The recesses 75 give the lens disc 25 a scalloped periphery which, as indicated in FIGS. 1 and 3, also aid in manually turning the disc.

From the foregoing description it will be apparent that the invention provides a novel and very advantageous ophthalmoscope construction. As will be understood by those familiar with the art, the invention may be embodied in other specific forms without departing from the spirit or essential characteristics thereof.

I claim:

1. In an ophthalmoscope, a housing having a viewing passage therethrough, a first and a second lens disc rotatably mounted in the housing, said discs having a common axis of rotation and being independently and directly manually rotatable in the clockwise or counter clockwise direction and arranged so that a lens in each disc is always in registry with the axis of the viewing passage, the first lens disc having a relatively large number of lenses of different diopters, the second lens disc having a relatively small number of lenses that are adapted to coact with the lenses of the first disc to greatly expand the total number of different lens diopters beyond the number provided by the first disc, the lenses of the two discs being able to coact in this manner when one lens in each disc is in registry with the viewing passage, and cam means in the housing that permits manual rotation of either said disc in either direction and coacts with the first and second lens disc, the cam means being operable after the first lens disc has been rotated through a predetermined angular distance to automatically pivot the second lens disc so that its lens in registry with the viewing passage is replaced by an adjacent lens, said cam means including a drive pin mounted on said first lens wheel, a cam member pivotally mounted on a pivot in the housing and having a member remote from said pivot engaging said second lens wheel across the axis of said lens wheels from said pivot, and a plurality of cam surfaces disposed on said cam member between said pivot and said engaging member and cammed by said pin to move said engaging member and said second disc during a portion of the rotation of the first disc.

2. An ophthalmoscope as defined by claim 1 wherein the first lens disc has twenty-three lenses that differ from one another by one diopter steps, and the second lens disc has three lenses the intermediate one of which is zero diopters.

3. An ophthalmoscope as defined by claim 2 wherein the twenty-three lenses in the first lens disc range from $-7$ to $+15$ diopters, and the three lenses in the second lens disc are a $-23$ diopter lens, a zero diopter lens and a $+23$ diopter lens.

4. An ophthalmoscope as defined by claim 1 wherein the first and second lens discs are spaced apart and the cam means is located between them.

5. An ophthalmoscope as defined by claim 4 wherein the cam means is a plate element pivotally connected to the housing, the plate element having a plurality of cam surfaces, and means on the first lens disc adapted to coact with the cam surfaces to cause pivotal movement of the plate element.

6. An ophthalmoscope as defined by claim 5 together with means interconnecting the cam means with the second lens disc whereby pivotal movement of the plate element causes corresponding pivotal movement of the second lens disc.

7. In an ophthalmoscope, a housing having a viewing passage therethrough, a first and a second lens disc rotatably mounted in the housing, said discs having a common axis of rotation and being independently rotatable by direct manual actuation in the clockwise and counter clockwise directions, each lens disc having a plurality of different lenses that are selectively movable into registry with the viewing passage, the first disc having a relatively large number of lenses with successively larger diopters, the second lens disc having a relatively small number of lenses that are adapted to coact with the lenses of the first lens disc to provide a combination of substantially greater number of different lens diopters than are provided by the first lens disc, the lenses of the two discs combining in this manner when a selected lens in each disc is in registry with the viewing passage, and a cam movement in the housing including a cam plate pivotally mounted to the housing by a pivot, the cam plate having a plurality of cam surfaces and being located between the first and second lens discs in close proximity to each, pin means affixed on the first lens disc to coat with the cam surfaces to cause pivotal movement of the cam plate, means on said cam plate remote from said pivot and beyond said cam surfaces engaging the second lens disc permitting the first and second lens discs to be rotated independently and whereby pivotal movement of the cam plate causes corresponding pivotal movement of the second lens disc.

8. An ophthalmoscope as defined in claim 7 wherein the first lens disc has twenty-three lenses that differ from one another by one diopter steps, and the second lens disc has three lenses the intermediate one of which is zero diopters.

9. An ophthalmoscope as defined in claim 8 wherein the twenty-three lenses in the first lens disc range from $-7$ to $+15$ diopters, and the three lenses in the second lens disc are a $-23$ diopter lens, a zero diopter lens and a $+23$ diopter lens.

10. An ophthalmoscope as defined in claim 9 wherein the first and second lens discs in combination provide sixty-nine different diopters ranging from $-30$ to $+38$ in one diopter steps.

11. An ophthalmoscope as defined in claim 7 together with a detent in the housing for releasably holding a selected lens in each lens disc in registry with the viewing passage, the detent having two spring arms one of which is adapted to engage each disc.

12. An ophthalmoscope as defined in claim 7 together with means in the housing to indicate the diopter number of the lens combination in registry with the viewing passage.

13. An ophthalmoscope as defined in claim 12 wherein the diopter indicating means includes a film bearing the diopter numbers, the film being mounted on the first lens disc.

14. An ophthalmoscope as defined in claim 13 wherein the film is opaque and the diopter numbers are translucent.

15. An ophthalmoscope as defined by claim 5 wherein said means on the first lens disc includes a pin protruding from a surface of said first lens disc, and said cam plate element has a plurality of raised portions defining between adjacent ones thereof channels which operatively engage said pin.

16. An ophthalmoscope as defined in claim 12 wherein said diopter numbers are arranged in concentric rows on a disc that rotates with said first lens disc, and said means to indicate the diopter number includes a window which moves with said cam means to register with a respective one of said rows.

17. An ophthalmoscope as defined in claim 8 wherein said second lens disc is limited in rotation to the positions of the first and third of its three lenses.

18. An ophthalmoscope as defined in claim 1, wherein said second lens disc is provided with a serrated lug at its periphery and serving as manually actuable means to effect independent rotation of said second lens disc.

19. An ophthalmoscope as defined in claim 1, wherein said second lens disc is provided with a pair of oppositely disposed serrated lugs at the periphery of the second lens disc and providing means to effect independent rotation of said second lens disc from either side of the ophthalmoscope housing.

20. An ophthalmoscope as defined in claim 19, wherein said lugs are disposed at the periphery of the first lens disc such that said lens discs can each be rotated without change of hand positions on the ophthalmoscope housing.

21. An ophthalmoscope as defined in claim 7, wherein said cam plate has its pivot and its engaging means disposed diametrically opposite one another with respect to said common axis of rotation.

22. An ophthalmoscope as defined in claim 1, wherein the channels of said cam member are open at each end thereof to admit said pin from either the clockwise or the counterclockwise direction.

* * * * *